(12) United States Patent
Caramuta (10) Patent No.: US 8,545,197 B2
(45) Date of Patent: Oct. 1, 2013

(54) PUMP, ESPECIALLY FOR BLOOD TREATMENT

(75) Inventor: Canio Caramuta, Salerno (IT)

(73) Assignee: Medical Service S.R.L., Salerno (IT)

( * ) Notice: Subject to any disclaimer, the term of this patent is extended or adjusted under 35 U.S.C. 154(b) by 0 days.

(21) Appl. No.: 11/887,179

(22) PCT Filed: Mar. 29, 2006

(86) PCT No.: PCT/IT2006/000196
§ 371 (c)(1),
(2), (4) Date: Sep. 26, 2007

(87) PCT Pub. No.: WO2006/103712
PCT Pub. Date: Oct. 5, 2006

(65) Prior Publication Data
US 2009/0016915 A1    Jan. 15, 2009

(30) Foreign Application Priority Data

Mar. 30, 2005  (IT) .............................. BO2005A0203

(51) Int. Cl.
*F04B 43/12* (2006.01)
(52) U.S. Cl.
USPC ....................... 417/477.2; 417/474
(58) Field of Classification Search
USPC ............... 417/477.1, 477.2, 474, 3; 604/4.01
See application file for complete search history.

(56) References Cited

U.S. PATENT DOCUMENTS

| | | | | |
|---|---|---|---|---|
| 3,518,033 A | * | 6/1970 | Anderson | 417/478 |
| 4,014,318 A | | 3/1977 | Dockum et al. | |
| 4,047,844 A | * | 9/1977 | Robinson | 417/3 |
| 4,060,348 A | * | 11/1977 | Della Bianca | 417/475 |
| 4,617,014 A | * | 10/1986 | Cannon et al. | 604/67 |
| 4,867,744 A | | 9/1989 | Borsanyi | |
| 5,011,378 A | * | 4/1991 | Brown et al. | 417/360 |
| 5,151,019 A | * | 9/1992 | Danby et al. | 417/474 |
| 5,165,873 A | * | 11/1992 | Meijer | 417/474 |
| 5,257,917 A | * | 11/1993 | Minarik et al. | 417/475 |
| 5,643,205 A | * | 7/1997 | Utterberg | 604/80 |
| 5,924,852 A | * | 7/1999 | Moubayed et al. | 417/474 |
| 5,935,106 A | * | 8/1999 | Olsen | 604/153 |
| RE37,074 E | * | 2/2001 | Danby et al. | 417/474 |
| 6,267,570 B1 | * | 7/2001 | Armando | 417/478 |
| 6,435,175 B1 | * | 8/2002 | Stenzler | 128/200.14 |
| 6,692,241 B2 | * | 2/2004 | Watanabe et al. | 417/477.2 |
| 2003/0190246 A1 | * | 10/2003 | Corwin et al. | 417/479 |
| 2005/0027231 A1 | * | 2/2005 | Kirchhof | 604/4.01 |
| 2005/0263207 A1 | * | 12/2005 | Karasawa et al. | 141/67 |

FOREIGN PATENT DOCUMENTS

WO    WO 2004020171 A1 *  3/2004

* cited by examiner

*Primary Examiner* — Peter J Bertheaud
*Assistant Examiner* — Dnyanesh Kasture
(74) *Attorney, Agent, or Firm* — The Webb Law Firm (57) ABSTRACT

The invention relates to a pump, especially usable as a peristaltic pump in an apparatus for blood treatment, wherein it is provided with at least a hammer element which interacts with at least one tube portion in which a fluid to be pumped flows and with motion means for said hammer element which push the hammer element against said tube portion so as to press it, the value of the stroke executed by said element not allowing the complete crushing of the tube itself.

3 Claims, 7 Drawing Sheets

PUMP, ESPECIALLY FOR BLOOD TREATMENT

The present invention relates to a pump which can be used, in particular, for blood treatment.

This invention can be used, together with a disposable cartridge or module, with a blood treatment apparatus in order to define a blood treatment system.

The present invention is suitable for being used in a medical/hospital field and, in particular, it relates to the problem of the setting of the machines used for dialysis, haemofiltration, decapneization or blood oxygenation and, generally speaking, for all the apparatus which comprise one or more peristaltic pumps and/or syringe pumps and which need complicated operations for placing the underpump tubes in their correct operating positions, for placing in their holders blood filters, oxygenators and other circuit components connected to one another by means of a complex flexible tube connection network, drip caps, devices for eliminating blood blisters, pressure sensors, temperature sensors, heaters and so on.

One of the aims of the present invention is providing a pump which allows a much more linear and homogeneous exit flux than in current peristaltic devices as well as an extremely reduced hemolysis; among the aims there are: simplifying the functioning and the start of well known procedures in a shorter time; limiting the risk of assembly mistakes; moreover it is possible to limit the need of highly qualified personnel and to obtain advantages such as a reduction of the priming volume thanks to the optimization and to the shortness of connections and to use rigid connection tubes without toxic plasticizers (phthalates) which are more biocompatible in general, as well to obtain a reduced hemolysis due to the functioning of the peristaltic pump. Therefore, the aim of the present invention is eliminating the above mentioned inconveniences.

According to the invention, these results have been achieved by adopting the idea of a pump having the features described in the independent claims. Further features are the subject of the dependent claims.

One of the advantages of the present invention is the pumping of blood with a very high homogeneity and reduced hemolysis; the preparation procedures and the starting of the apparatus for blood treatment a are remarkably simplified; the risk of mistakes is basically eliminated; this apparatus can be used by personnel which is not highly qualified and the priming is remarkably reduced; it offers a system consisting of a disposable cartridge characterized by a high biocompatibility.

Each technician who works in this field will understand these advantages and further advantages of the present invention thanks to the following description and to the enclosed drawings as a practical exemplification of the invention, which should not be considered in a limitative sense, wherein:

A possible example of a system consisting of an apparatus and of a disposable cartridge or module according to the invention is described in the following, with an initial reference to FIGS. 1-6;

The term module or cartridge used in the present description refers to a disposable container 1 with at least one rigid wall or portion 2 which contains: the components necessary for the treatment procedure and for the corresponding internal connections; pre-positioned connections or connections which are assembled with those external to the patient as well as for any sub-containers for waste products to be eliminated; the mechanical support of the under-pump tubes (understood as a reaction plane of the frontal access peristaltic pumps contained in the base apparatus for blood treatment). All the internal components of the disposable cartridge and the external connections are preassembled, so as to be ready for use.

In particular, the disposable cartridge 1 which can be made of transparent and rigid plastic material, is provided with fixing means for apparatus 3 (also called base 3 in the present description) which allow an operating connection capable of exchanging data with the temperature and pressure sensors, with air bubble detectors, blood blisters detectors and so on, but also of allowing the liquids contained or passing through disposable cartridge 1 to be moved by means of a system of "frontal access peristaltic pumps" which do not require a manual operation for their preparation and can function as soon as they are connected to cartridge 1.

Figure 1:
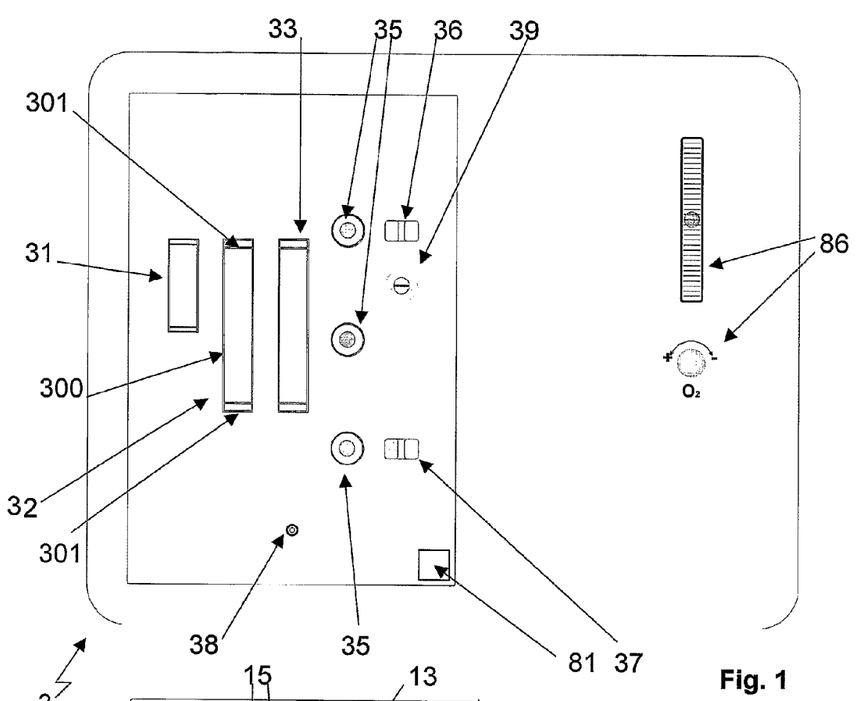
FIG. 1 shows a possible embodiment of an appliance for blood treatment according to the present invention, schematically shown in a front view.
Figure 2:
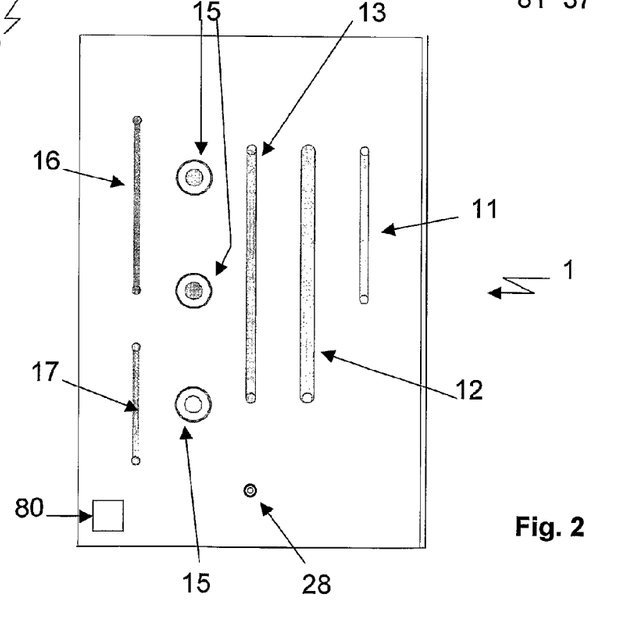
FIG. 2 shows a possible embodiment of a disposable cartridge or module according to the present invention, schematically shown and in a partial front view.
Figure 3:
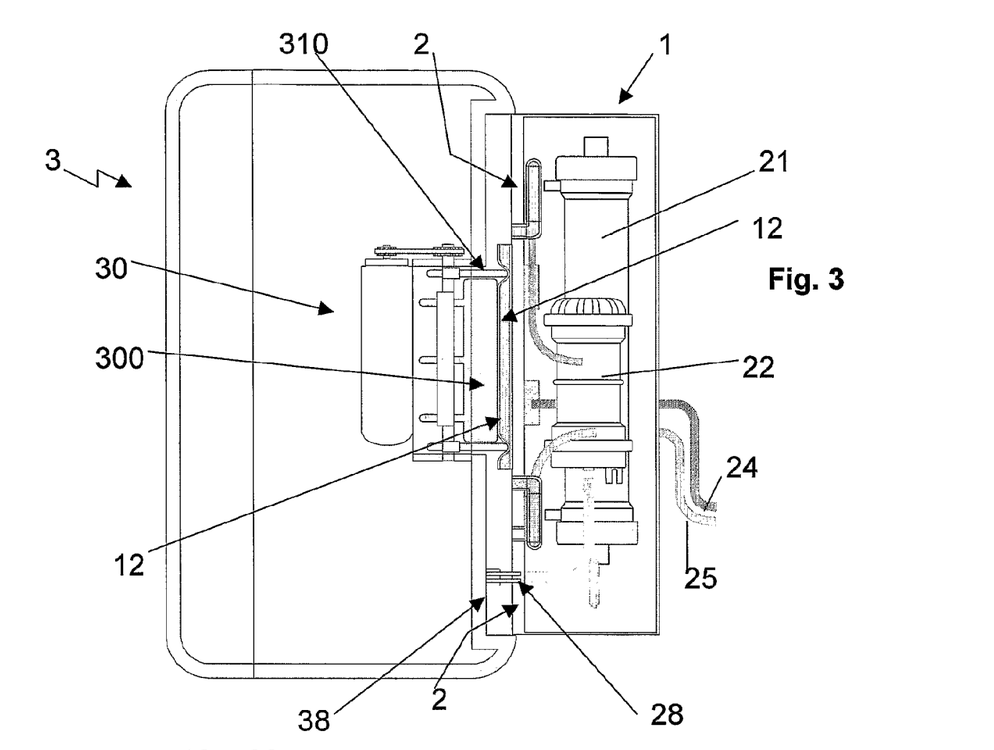
FIG. 3 is a schematic section view of the appliance of FIG. 1 placed in front of the disposable cartridge of FIG. 2, with the cartridge shown in a more complete configuration, that is provided with more components than that in FIG. 2.
Figure 4:
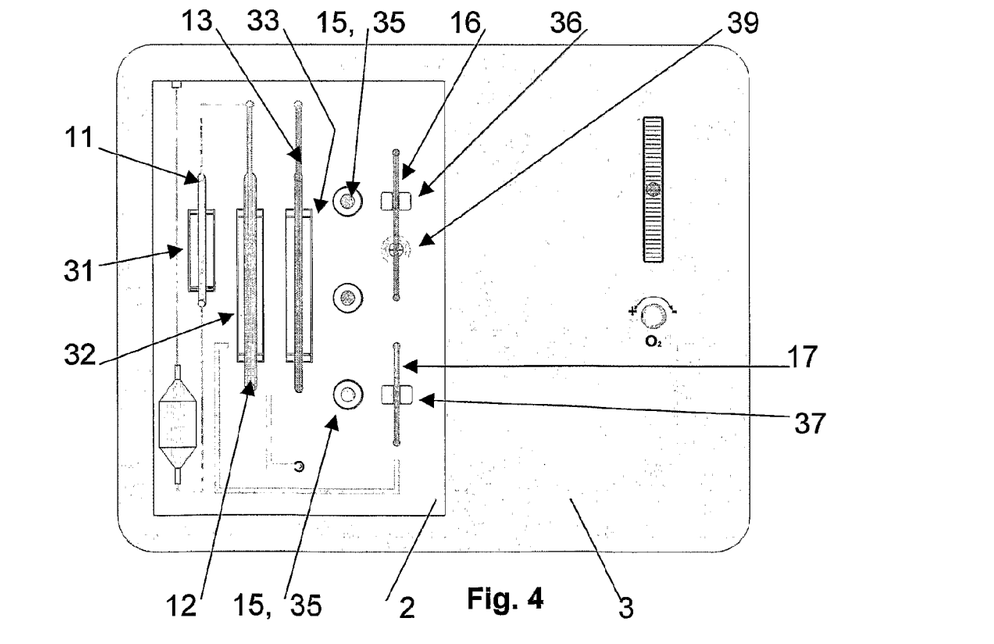
FIG. 4 shows the view in FIG. 1, in which some components of the disposable cartridge of FIG. 2 have schematically been associated with the apparatus.

Cartridge 1 can be provided with an identification element which allows a given cartridge to be associated with a corresponding treatment procedure. For example, disposable cartridge 1 can be provided with an identification element which allows the association of a given cartridge with a corresponding treatment procedure. For example, disposable cartridge 1 can be provided with a chip or with a similar device interacting with a corresponding reader placed on base 3. The reader placed on base 3 can emit a corresponding consensus or error signal and, if necessary, indicate, for example in a screen, the parameters of the treatment to be executed. This allows a further reduction of possible errors when preparing the appliance for blood treatment. In FIG. 2 the identification element on disposable cartridge 1 is schematically represented by a rectangle 80, while rectangle 81 of FIG. 1 represents the reader of base 3. Identification element 80 and corresponding reader 81 can be replaced with particular structures of the disposable cartridge and of the base, which allow the coupling of the two parts of the blood treatment system. For example it is possible to provide a male-female association with a particular shape and/or dimensions of the elements which fit with one another so that the base can recognise the cartridge suitable for the foreseen treatment which has been set.

In the non limitative example shown in the figures, base 3 is provided with three front access peristaltic pumps 31, 32, 33. Three corresponding tube portions 11, 12, 13 are present on disposable cartridge 1 which are in contact with said pumps 31, 32, 33, when disposable cartridge 1 is associated with base 3. In practice, in the non-limitative example shown in the drawings, disposable cartridge 1 features on one side (in the example the side with a greater surface) some tube segments 11, 12, 13 projecting from disposable cartridge 1. These tube segments are positioned adjacent to the disposable cartridge itself.

Some pressure or temperature transducers or transducers for other values to be measured, as well as other tube segments 16, 17 on which some clamps act, oxygen connectors or similar devices can be positioned near these tubes. According to the type of therapy to be carried out, disposable cartridge 1 is duly provided with suitable components such as filtering devices, measurers and so on. These devices are already well known and will not be described in detail. The transducers may consist of membranes acting on corresponding detectors positioned on the base, which are capable of exchanging data with the detectors. In practice, the membranes can define a physical connection (pneumatic or hydraulic) with the corresponding internal detector on the base.

With reference to the example illustrated, disposable cartridge 1 is provided with a filtering device for blood or haemofilter 21, with an hoxygenator device or decapneizator 22, with an oxygen connector 28 featuring a corresponding delivering device 38 positioned on base 3, as well as with two ducts 24 and 25 which allow the entry and exit connection with the patient under treatment according to a well known method. Once the disposable cartridge suitable for the therapy to be carried out has been chosen, by applying disposable cartridge 1 to appliance 3, frontal access pumps 31, 32, 33 contained in the apparatus will be coupled to tube segments 11, 12, 13 containing the liquids to be moved which are part of disposable cartridge 1; at the same time, pressure transducers 15 will be in contact with corresponding detectors 35 on base 3, the oxygen connector 28 will be coupled to the opening 38 of the delivering device, the "clamp" 39 of base 3 will be positioned in contact with tube segment 16 which is to be occluded, bubble and blood blister detectors will be positioned on the tube segment adjacent to it (the example schematically shows an air bubble detector acting on tube portion 16 and a blood blister detector 37 acting on tube portion 17) and the apparatus for filtering and removing carbon dioxide, at this point, after carrying out up the only connection of the disposable cartridge, can be started.

The apparatus or base is usually provided with a screen, which displays the possible procedures according to the disposable cartridge actually assembled, the parameters set, the correct functioning of the disposable cartridge, possible alarms and the possibility for the operator to vary the above parameters. It is possible to add accessories such as printers, connections to the network and so on. In FIG. 1, numerical reference 86 shows the adjustment means for the oxygen flow.

Disposable cartridge 1 can contain the components for measuring the different values, the connection tubes, the "active" components such as haemo-concentrators, oxygenators, haemofilters, dyalisis filters, possible control components such as droppers, de-bubblers, sub-containers to be filled with drugs (for example heparin).

Figure 8:
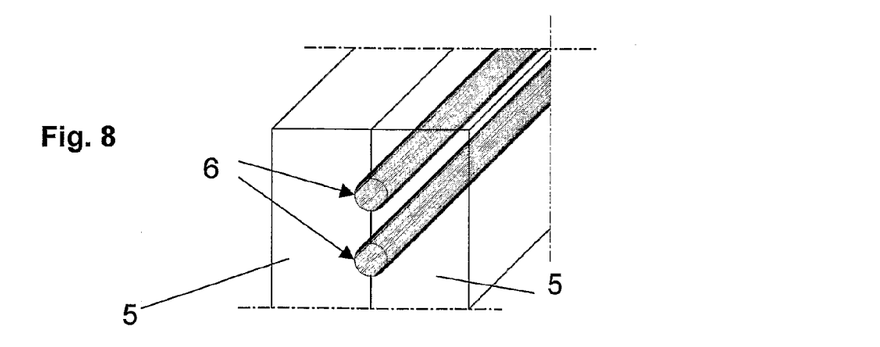
FIG. 8 is the scheme of a possible embodiment of ducts according to the present invention.

With reference to the example of FIG. 8, to obtain a further reduction of the priming volume and to render connections (ducts) more linear, some of the connections can be made by performing a passage between two correspondingly grooved plates of suitable material which are then glued to each other so as to form a circuit inside a "plate" for taking all the various liquids to the various components (internal or external components) like copper tracks in an electronic circuit. The schematic view of FIG. 8, numerical reference 5 indicates two associated plates which form two ducts 6.

As said above, frontal access peristaltic pumps allow the liquids to be moved through the tubes they are in contact with, without the action of the operator necessary in traditional pumps.

The example of FIGS. 1-6 shows peristaltic pumps 31, 32, 33 in which the so called "rotor" which presses on the tube, does not act against a surface which is part of the pump and in a radial direction in relation to the rotor itself, but it acts frontally (like a front cam) against the tube and against a rigid matching surface 2 which is part of disposable cartridge 1. In practice, each of pumps 31, 32, 33 is provided with a plurality of hammer elements 300, 301 placed along the longitudinal development of tube portions 11, 12, 13 and sequentially moved to engage the corresponding points of the tube portions, so as to obtain a peristaltic effect.

Figure 5:
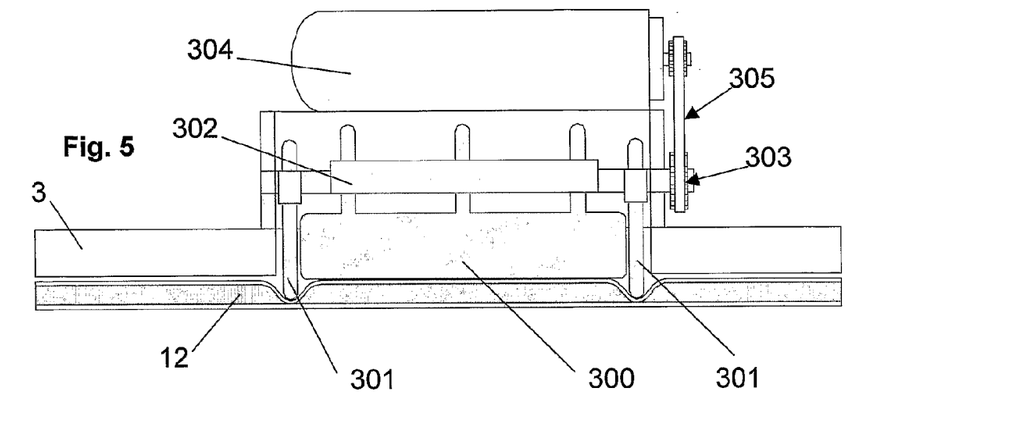
FIG. 5 is an enlarged schematic lateral view of the pump according to the present invention shown in FIG. 3.

In particular, for a better description of the functioning, FIG. 5 shows a linear pump (indicated with 30 and shown also in FIG. 3), which is provided with three hammer elements 300, 301. Pump 30 comprises a cam shaft 302 and three hammer elements 300, 301 with suitable dimensions which are placed side by side, that is to say they are overlapped when the pump is in a vertical position like in FIG. 3. In particular, the three hammer elements consist of a central element 300 which is longer, and of two lateral elements 301 which are shorter, one of which is placed upstream, while the other is placed downstream to element 300. The cam shaft features three different suitably shaped cams so as to internally detect hammer elements 300, 301 and to push them toward tube portion 12 or to move it away from it. In practice, cam shaft 302 (on which hammer elements 300, 301 are fitted) can be rotated by acting on one of its ends 303 by means of motor means (consisting of motor 304 connected to shaft 302 by means of belt 305) so as to sequentially push the three hammer elements 300, 301 against tube portion 12. Hammer elements 300, 301 suitably compress the tube portions of disposable cartridge 1 thanks to the presence of the rigid wall 2 which acts as an "anvil" or reaction plane for the hammer elements and which is part of disposable cartridge 1. In fact, central element 300, which is much longer than lateral elements 301 acts as real a pumping element while the two external elements 301 act as valves; in practice external elements 301 completely compress the tube so as to occlude it, while central element 300 crushes the tube only until a percentage value of nearly 90% without damaging the solid components of blood (especially erytrocytes) and reducing hemolysis in comparison with traditional peristaltic pumps.

Figure 6:
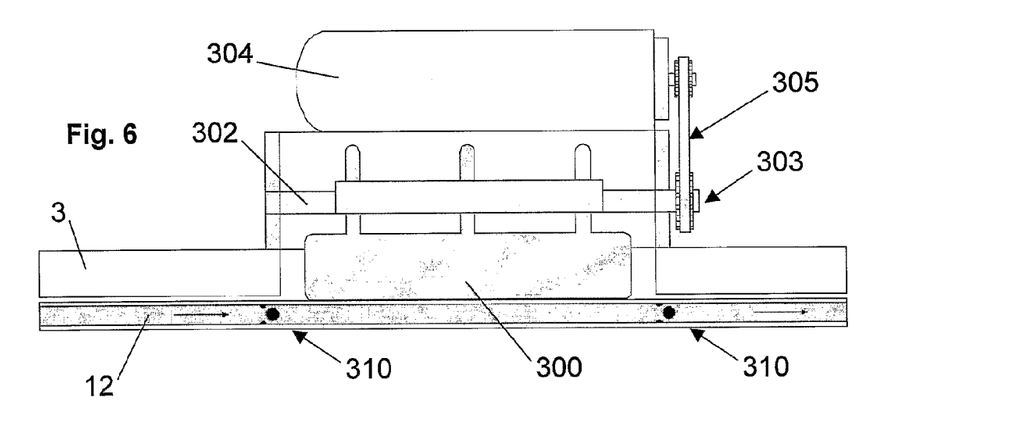
FIG. 6 is a schematic lateral view of another embodiment of a pump according to the present invention.

In an alternative embodiment shown in FIG. 6, the two external pump hammer elements are replaced with non return valves 310 (for example sphere valves) positioned at the beginning and at the end of the portion of under-pump tube 12; in this case the pump consists of a single hammer element 300.

Figure 9:
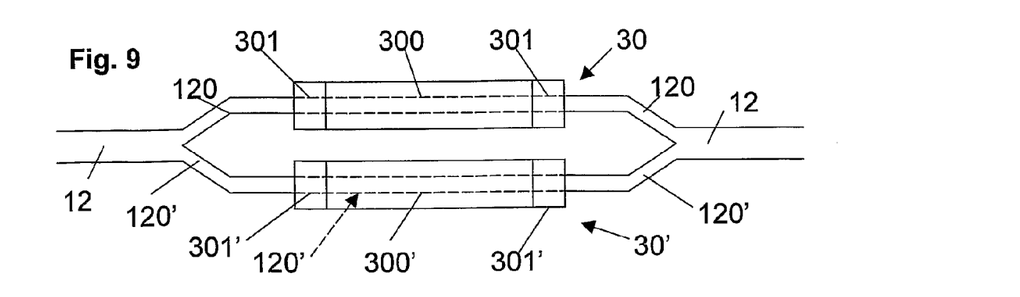
FIG. 9 schematically shows the positioning of a couple of pumps acting on a split tube portion.

FIG. 9 schematically shows a further embodiment of the invention, which consists of two pumps 30 and 30' acting on the portion of a split tube, that is a tube 12 which is split into two ducts 120 and 120' in one of its intermediate sections, which ducts, upstream and downstream to the area on which the pumps act, are joined again, so as to reform said tube 12. The two pumps 30 and 30' are reverse-phase operated so that their hammer elements 300, 301, 301' alternatively interact with corresponding tube portions 120 and 120'. In particular, pump 30 comprises a central hammer element 300 and the lateral elements 301'; correspondingly, pump 30' comprises a central hammer element 300' and the lateral elements 301'. In this way, instead of an intermittent pulsing action, it is possible to obtain a substantially continuous flux, in which the instantaneous flow is similar to the medium flux, so that it is possible to maintain the pressure values which the filters or other components can bear, in order to avoid damages due to a possible pressure peak or coagulations which can cause clots or other problems.

The examples of FIGS. 1-6 show the use of frontal access peristaltic pumps which develop linearly and are provided with hammer elements. According to the present invention, the pump can be "rotary" or "linear" depending on the fact that the pressure the pump exerts on the tube, so as to obtain a peristaltic effect, acts either on an arc of circumference or on a segment of a straight line (like in the example shown).

Figure 7:
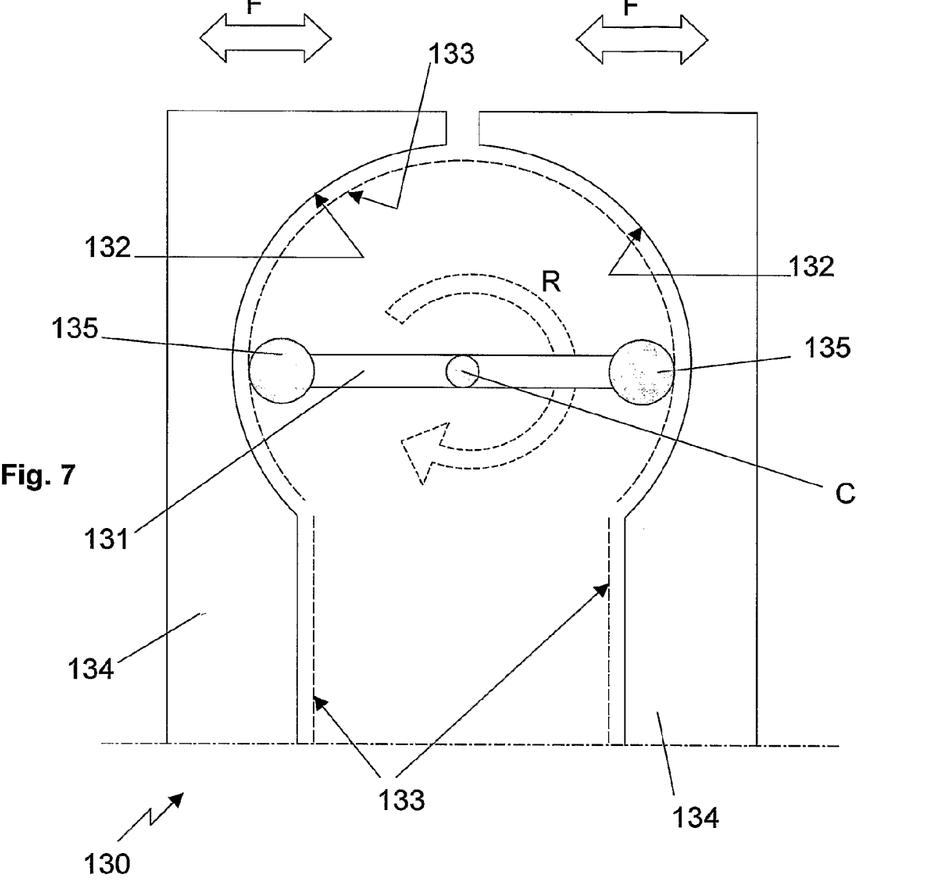
FIG. 7 is the scheme of an alternative embodiment of a frontal access peristaltic pump.

FIG. 7, instead, shows a frontal access peristaltic pump 130 which is not provided with the hammer elements described above but with a basically traditional rotor 131 acting on walls 132 presented by the pumps itself 130 so as to press, by means of two ends 135, a tube 133, schematically shown with dashed lines. Ends 135 can consist of rolls whose axis is parallel to rotation axis C of the body of rotor 131. In the usual way, the rotation (see arrow R) performed by rotor 131 determines the peristaltic effect which pushes the fluid contained in duct 133. In this embodiment, walls 132 are advantageously presented by two half bodies 134 which can be approached to each other or moved away from each other as indicated by arrows F. In order to allow a correct coupling to pump 130, the disposable cartridge is provided with a tube portion whose development allows its introduction between the ends 135 of rotor 131 and the walls 132, when the two half bodies 134 are far from each other. With reference to the example shown, the tube portion to be fixed to the disposable cartridge features a basically annular development, which is open at the bottom, with two arms extending downwards so as to fit the profile of walls 132. In other terms, said portion can be Ω shaped (omega). The tube portion projects from the corresponding face of disposable cartridge so that it can be inserted around rotor 151 by simply approaching the disposable cartridge to the base. In practice, when preparing the apparatus for blood treatment, half bodies 134 are placed away from each other and kept in this position until tube 133 is inserted around rotor 131; then, half bodies 134 are joined to each other so that walls 132 compress the tube at ends 135 of rotor 131. Once rotor 131 has been operated, the peristaltic pressure of the liquid contained in tube 133 starts.

Figure 12:
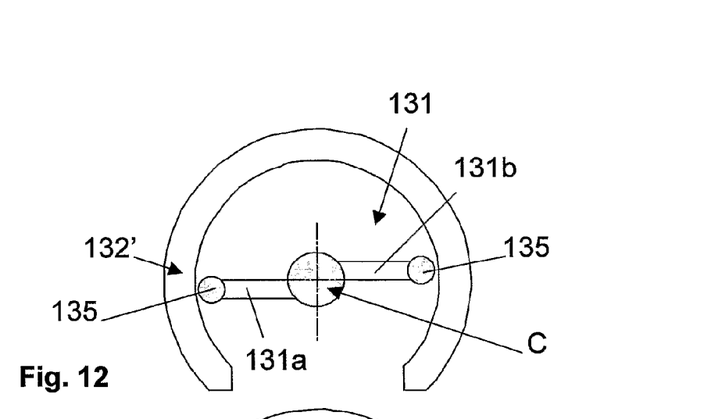
FIG. 12 is a schematic front view of a further embodiment of a pump according to the invention, shown in a maximum extension configuration.
Figure 13:
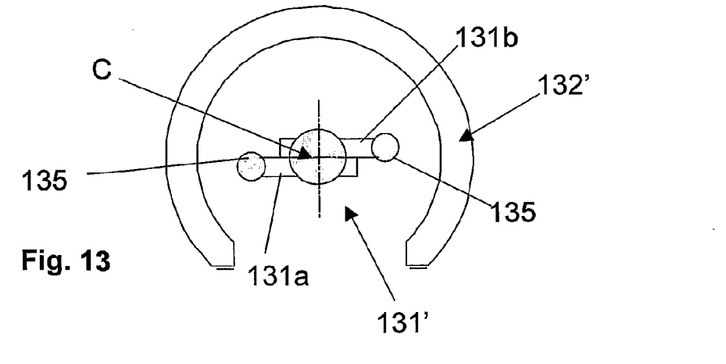
FIG. 13 shows the pump of FIG. 12 in a minimum extension configuration.

An alternative of said rotary peristaltic pump is schematically shown in FIGS. 12 and 13. In this case, rotor 131 consists of two arms 131a and 131b and it is capable of becoming "compact" (see FIG. 13) (for example telescope-like or pantograph-like) by reducing the extension of its arms 131a and 131b so as to allow the introduction of the under-pump tube and by keeping a fixed position of the wall (schematically shown by area 132' in the figures). Rotor 131 is capable of returning to its extended operating position (see FIG. 12) when the tube is in the correct position and the disposable cartridge is completely inserted on the base. Even in this case, the tube portion presented by disposable cartridge 1 can be basically "Ω" shaped.

The disposable cartridge which can be used for the examples of FIGS. 7, 12 and 13 can obviously be provided with the same components as those shown in the examples of FIGS. 1-6 in addition to a tube portion whose shape allows its positioning around the rotor. In other words, by simply bringing the disposable cartridge nearer to the apparatus, the latter will be ready for treatment.

Figures 10, 11:
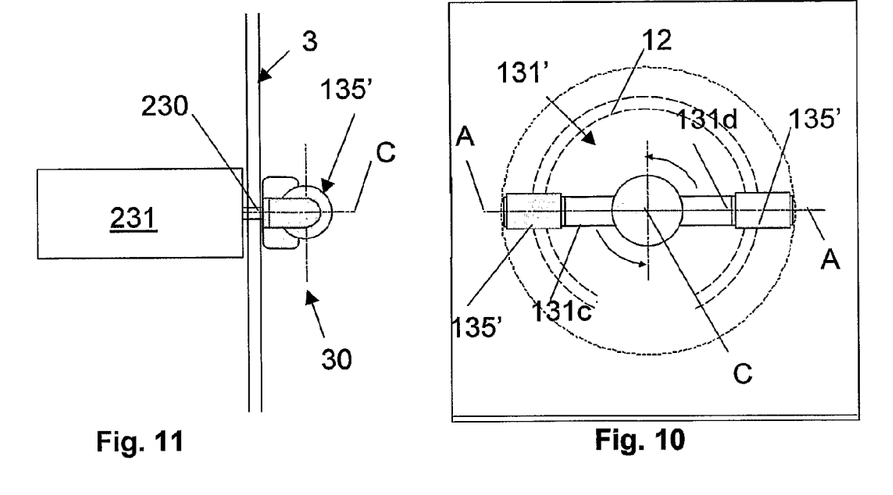
FIG. 10 is a schematic front view of a further embodiment of a pump according to the present invention.
FIG. 11 is a schematic lateral view of the example of FIG. 10.

FIGS. 10 and 11 schematically and partially show an embodiment of a frontal access peristaltic pump 30. The pump shown in FIGS. 10 and 11 consists of a rotor 131' capable of rotating around a corresponding axis C, which, in the example, coincides with shaft 230 of a motor 231 determining the rotation of rotor 131'. Rotor 131' consists of two arms 131c and 131d whose axes A are orthogonal to rotation axis C of the rotor, in a radial position. Rotor 131' is provided with two pressure elements 135' consisting of rotary cylinders whose axis coincides with axis A of arms 131c and 131d; in practice cylinders 135' can rotate around an axis which is radially positioned in relation to rotor 131' so as to interact on the front, that is to say with its cylindrical surface with tube portions presented by cartridge 1 which is coupled to a base 3 which presents said pump 30.

Tube portion 12, which is schematically shown with dashed lines in FIG. 10, obviously features an open-ring structure, that is according to an arc of circumference.

In this last embodiment, pump 30 is a rotary pump and the pressure elements are not the hammers 300, 301 described above with reference to the examples of FIGS. 1-6 and 9, but the two rotary cylinders featuring rotation axis (A) along the radiuses of the rotor and acting as a rotary frontal cam on tube 12. Even in this case, disposable cartridge 1, in addition to tube portion 12 shown in the figure, is provided with other components which are not shown in FIGS. 10 and 11 in order to simplify their explanation.

Figure 14:
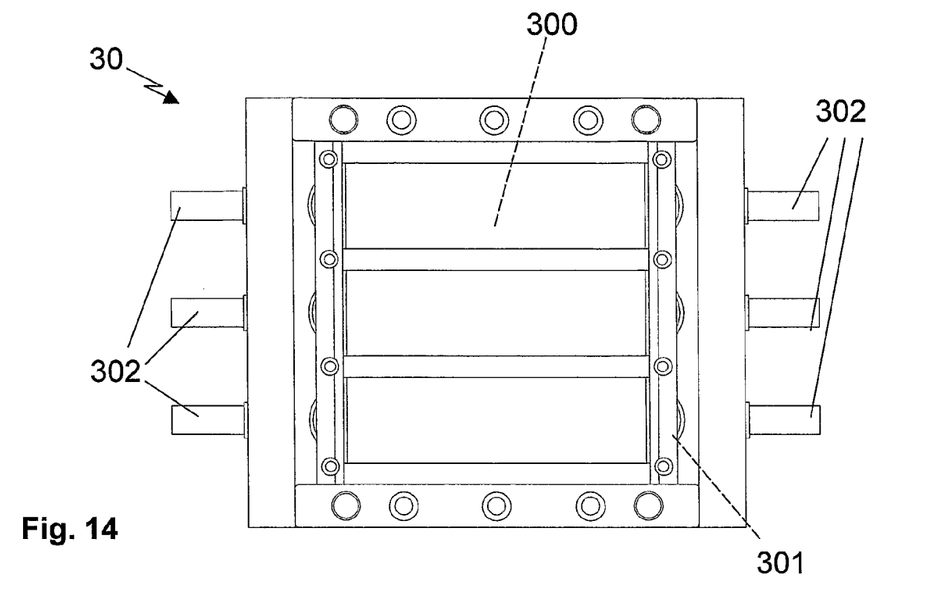
FIGS. 14, 15, and 16 schematically show a further embodiment of the pump of the invention, in different scales, which is respectively shown in a top plan view (FIG. 14), in a possible cross section view (FIG. 15) in a possible longitudinal section view (FIG. 16) rotated of 90° in comparison with the previous view.
Figure 15:
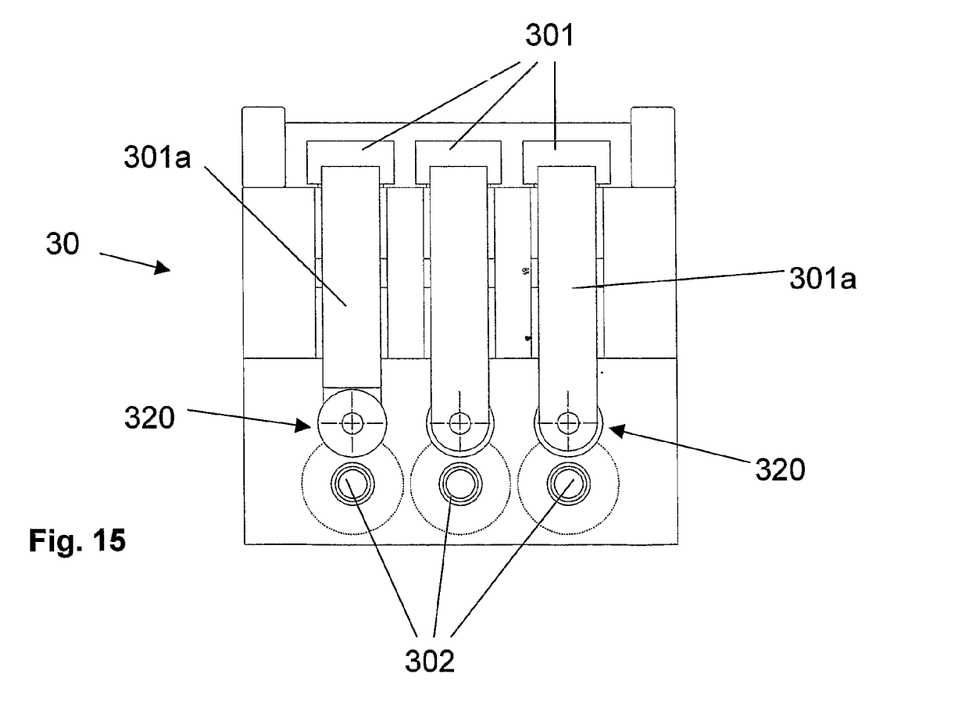
Figure 16:
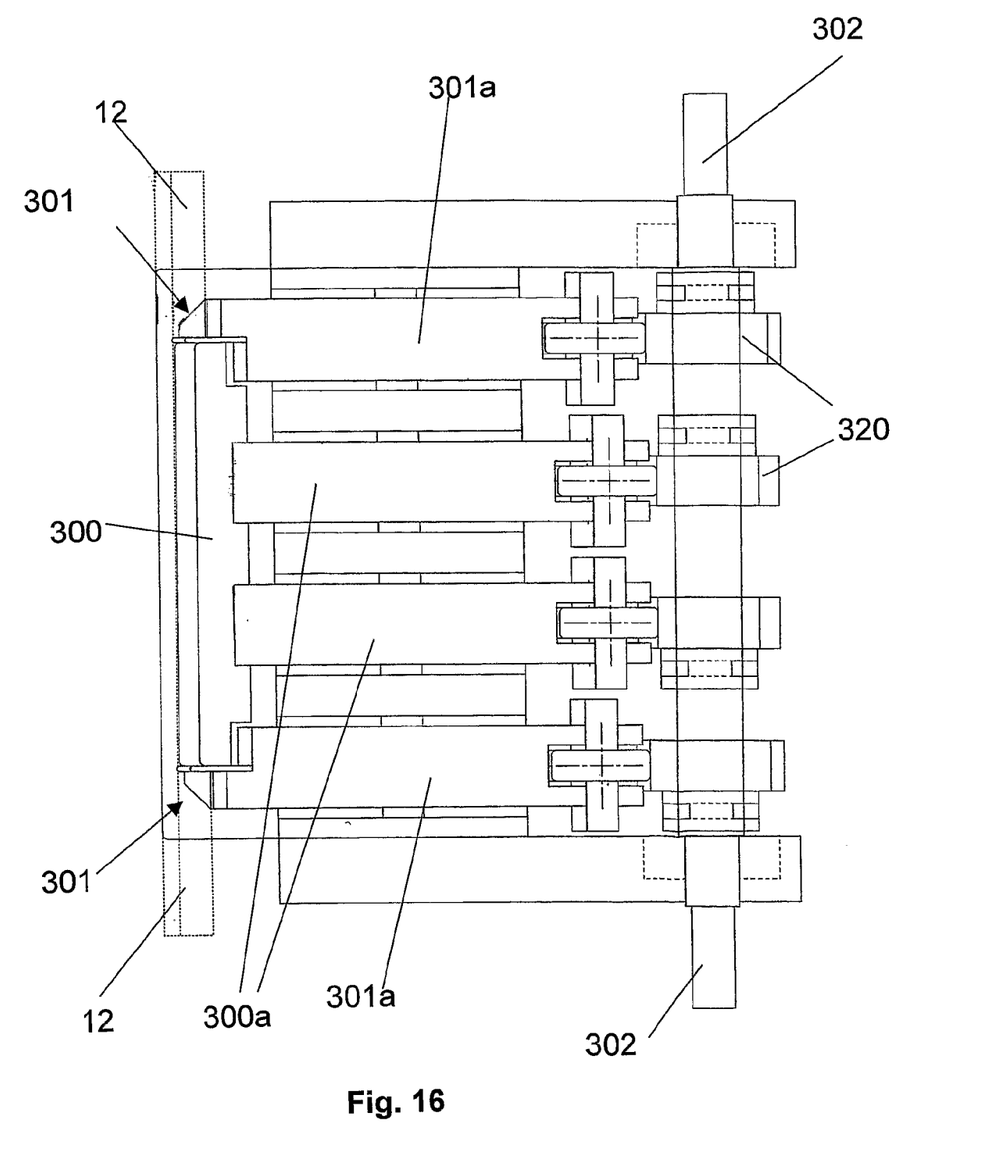

FIGS. 14-16 show a further embodiment of a pump according to the invention, which can be used for pumping on three different tube portions which are parallel to one another.

In particular, pump 30 has three cam shafts 302 on which hammer elements 300 and 301 are mounted. In the example shown in the figures cams 320 are fitted on shaft 302, to which two lateral elements 301a and two central elements 300a are connected. Cam shafts 302 are connected to motion means which are not shown in the figures.

Central elements 300a are joined to a single central hammer element 300 at their distal end. This solution guarantees an excellent balance of the thrust of hammer 300 on tube 12 which is shown in FIG. 16 with dashed lines.

The two lateral elements 301 bear lateral hammer elements 301 on the corresponding distal ends, that is those elements defining a kind of valve upstream to and downstream to central element 300.

The profiles of the two lateral hammer elements 301 are advantageously identical but differentiated of 180°, that is symmetrical. In particular, the profile of each lateral hammer element features an inward inclined structure that is in the direction of central hammer element 300.

The particular structure of lateral hammer elements 301 allows the gradual and quick crushing of tube 12 so as to avoid damaging the solid components of blood. As shown more in detail in FIG. 14, pump 30 is provided with three hammer units, and each of them features the structure described above with reference to FIG. 16; in this way, it is possible to carry out pumping on three different tube portions. The action on the various tube portions can be modified by varying the action of cam shafts 302 on hammer elements 300, 301.

The basic concept of the present invention is that of manufacturing a frontal access pump which can be coupled to a disposable cartridge, in which the position and the structure of the various active and passive components allows their direct coupling to the corresponding parts of the base apparatus. So, the base apparatus can be provided with one or more frontal access peristaltic pumps, with pressure elements which can be coupled to one ore more tube portions presented by the disposable cartridge, as said pumps can be "rotary" or "linear" pumps as specified above. In the same way, the base apparatus can be provided with one or more frontal access peristaltic pumps provided with a rotor and mobile walls, (or with a "collapsable" rotor) which can be coupled with one or more corresponding tube portions whose structure allows their positioning around the rotor when the disposable cartridge is couple to the apparatus. In all the above non limitative cases the apparatus and the disposable cartridge can be provided with additional pumps, ducts, measuring and filtering devices, oxygenators and so on, whose structure allows the immediate starting of the apparatus without the complex preparation procedures of the well known technique.

The control devices of the elements described above, which are shown in the enclosed drawings, are known to the technicians who work in this field and, for this, reason, they have not been described in detail in order to simplify their explanation. Moreover, the execution details may vary as regards the shape the size, the arrangement of the elements, the kind of material used, but they are within the limits of the solution adopted and within the limits of the protection offered by the present patent.

The invention claimed is:

1. An apparatus for blood treatment, comprising a base provided with a linear pump and a disposable cartridge provided with a plurality of components necessary for the treatment procedure, with at least one tube portion for the fluid to be pumped and with a rigid wall, wherein said pump comprises:
   at least one pumping body, the at least one pumping body being provided with a first hammer element which interacts with said at least one tube portion, pressing the same at least one tube portion against said rigid wall of the disposable cartridge, an additional hammer element positioned upstream to said first hammer element, and another additional hammer element positioned downstream to said first hammer element;
   a motion mechanism for said first hammer element and for said two additional hammer elements, which sequentially pushes said first hammer element and said two additional hammer elements against said at least one tube portion so as to sequentially be moved to engage corresponding points of said at least one tube portion so as to obtain a peristaltic effect, the value of the stroke executed by said first hammer element not allowing the complete pressing of said at least one tube portion itself and preventing the contact between inner walls of said at least one tube portion, and the value of the stroke executed by said additional hammer elements allowing the complete pressing of the tube itself so as to occlude the at least one tube portion;
   said first hammer element being longer than said two additional hammer elements so to define two valves by means of the action of said two additional hammer elements, respectively downstream and upstream;
   wherein said disposable cartridge is formed by a container which defines said rigid wall and which contains the components necessary for a treatment procedure and for the corresponding internal connections; said components of the disposable cartridge and said connections being preassembled, so as to be ready for use, allowing the starting of the blood treatment by means of the direct association of said disposable cartridge to said linear pump;
   wherein said at least one tube portion projects from said disposable cartridge, so as to be ready to be placed in correspondence of said hammer element and said additional hammer elements;
   wherein said at least one tube portion of the disposable cartridge is split into two or more ducts in a section of said at least one tube portion, said ducts, upstream and downstream to the area on which the pump acts, being joined again, so as to re-form said at least one tube portion, and wherein the pump comprises two or more pumping bodies acting on said two or more ducts, said pumping bodies being reverse-phase operated so that their hammer elements alternatively interact with corresponding ducts, in order to obtain a continuous flux;
   wherein said components necessary for a treatment procedure contained by said disposable cartridge comprise at least a hemofilter and an oxygenator device; and
   wherein said disposable cartridge is provided with an identification element which can be unequivocally associated with a corresponding element of said base.

2. The apparatus of claim 1, wherein said identification element is a chip and said corresponding element is a chip reader.

3. The apparatus of claim 1, wherein said additional hammer elements are provided with symmetrical profiles.

* * * * *